US012303502B2

(12) United States Patent
Bafna et al.

(10) Patent No.: US 12,303,502 B2
(45) Date of Patent: May 20, 2025

(54) ORAL LIQUID COMPOSITION COMPRISING IVACAFTOR

(71) Applicant: Kinedexe UK Limited, Middlesex (GB)

(72) Inventors: Vardhaman Chandrakant Bafna, Maharashtra (IN); Mahesh Mohanrao Bhadgale, Maharashtra (IN); Mokshada Milind Vable, Maharashtra (IN); Sweety Rajbahadur Singh, Maharashtra (IN)

(73) Assignee: KINEDEXE UK LIMITED, Hayes (GB)

( * ) Notice: Subject to any disclaimer, the term of this patent is extended or adjusted under 35 U.S.C. 154(b) by 897 days.

(21) Appl. No.: 17/593,430

(22) PCT Filed: Apr. 16, 2020

(86) PCT No.: PCT/IB2020/053602
§ 371 (c)(1),
(2) Date: Sep. 17, 2021

(87) PCT Pub. No.: WO2020/212898
PCT Pub. Date: Oct. 22, 2020

(65) Prior Publication Data
US 2022/0160698 A1    May 26, 2022

(30) Foreign Application Priority Data
Apr. 18, 2019  (IN) .............................. 201921015579

(51) Int. Cl.
*A61K 31/47* (2006.01)
*A61K 9/00* (2006.01)
*A61K 9/08* (2006.01)
*A61K 47/10* (2017.01)
*A61K 47/14* (2017.01)
*A61K 47/20* (2006.01)
*A61K 47/26* (2006.01)
*A61K 47/44* (2017.01)

(52) U.S. Cl.
CPC ............ *A61K 31/47* (2013.01); *A61K 9/0053* (2013.01); *A61K 9/08* (2013.01); *A61K 47/10* (2013.01); *A61K 47/14* (2013.01); *A61K 47/20* (2013.01); *A61K 47/26* (2013.01); *A61K 47/44* (2013.01)

(58) Field of Classification Search
CPC ............................. A61K 31/47; C07D 215/56
USPC ......................................................... 514/312
See application file for complete search history.

(56) References Cited

U.S. PATENT DOCUMENTS

| | | | |
|---|---|---|---|
| 7,553,855 B2 | 6/2009 | Young et al. | |
| 8,163,772 B2 | 4/2012 | DeMattei et al. | |
| 8,324,242 B2 | 12/2012 | Ruah et al. | |
| 8,354,427 B2 | 1/2013 | Van Goor | |
| 8,471,029 B2 | 6/2013 | Arekar et al. | |
| 8,629,162 B2 | 1/2014 | Hadida-Ruah et al. | |
| 8,674,108 B2 | 3/2014 | Luisi et al. | |
| 8,754,224 B2 | 6/2014 | Hurter et al. | |
| 8,883,206 B2 | 11/2014 | Dokou et al. | |
| 2006/0074075 A1 | 4/2006 | Hadida-Ruah et al. | |
| 2014/0221424 A1 | 8/2014 | Zha | |
| 2015/0010628 A1 | 1/2015 | Dokou et al. | |

FOREIGN PATENT DOCUMENTS

| | | | |
|---|---|---|---|
| WO | WO-2012027731 A2 | 3/2012 | |
| WO | WO-2016199085 | 11/2012 | |
| WO | WO 2017/187340 A1 * | 2/2017 | |
| WO | WO-2020212898 A1 * | 10/2020 | ............. A61K 31/47 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Chapter 1: Pharmaceutical Solutions for Oral Administration, https://www.Pharmpress.com/files/docs/FT_pharm_dosage_sample.pdf, May 7, 2008, Chapter 1, pp. 1-24.
International Search Report issued in PCT/IB2020/053602 on Jul. 14, 2020.

* cited by examiner

*Primary Examiner* — Douglas M Willis
(74) *Attorney, Agent, or Firm* — Blank Rome LLP

(57) ABSTRACT

The present invention provides a stable oral liquid solution composition comprising ivacaftor or a pharmaceutically acceptable salt or solvate thereof and a solvent system selected from the group consisting of Polyethylene Glycols 400 and/or Hydrogenated Vegetable Oil used individually or in combination thereof. The invention also provides a method for treating or lessening the severity of cystic fibrosis is provided.

25 Claims, No Drawings

ORAL LIQUID COMPOSITION COMPRISING IVACAFTOR

CROSS-REFERENCE TO RELATED APPLICATIONS

This application is the U.S. national stage of International Patent Application No. PCT/IB2020/053602, filed Apr. 16, 2020, which claims the benefit of Indian complete application number 201921015579 dated 18 Apr. 2019 entitled, 'Pharmaceutical Oral Liquid Solution of Ivacaftor', the contents of which are incorporated herein by reference.

FIELD OF THE INVENTION

The present invention relates to stable oral liquid solution comprising ivacaftor or a pharmaceutically acceptable salt or solvate thereof and solvent system selected from the group essentially of polyethylene glycols or hydrogenated vegetable oil or mixture thereof.

BACKGROUND OF THE INVENTION

Ivacaftor is classified as a cystic fibrosis transmembrane conductance regulator (CFTR) potentiator and is indicated for the treatment of cystic fibrosis (CF) in patients who have a G551D mutation in the CFTR gene. Ivacaftor is a white powder with a low aqueous solubility and the bioavailability of Ivacaftor is significantly enhanced when co-administered with food. Ivacaftor is chemically known as N-(2,4-di-tert-butyl-5-hydroxyphenyl)-1,4-dihydro-4-oxoquinoline-3-carboxamide and is represented by compound of structural formula I. Ivacaftor is having an empirical formula of $C_{24}H_{28}N_2O_3$ and a molecular weight of 392.499 g/mol.

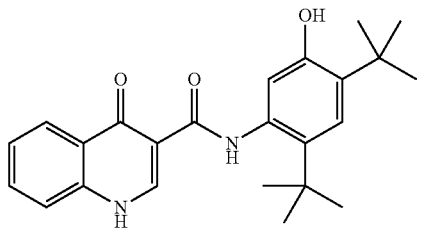

Formula I

Cystic fibrosis (CF) is a recessive genetic disease that affects approximately 30,000 children and adults in the United States, approximately 30,000 children and adults in Europe, and more than 70,000 people worldwide. Despite progress in the treatment of CF, there is no cure. Approximately 1000 new cases of CF are diagnosed each year, more than 75 percent of people with CF are diagnosed by age of 2, and more than half of the CF population is age 18 or older. CF is caused by mutations in the cystic fibrosis transmembrane conductance regulator gene (CFTR) that encodes an epithelial chloride ion channel responsible for aiding in the regulation of salt and water absorption and secretion in various tissues. Small molecule drugs, known as potentiator that increase the probability of CFTR channel opening, represent one potential therapeutic strategy to treat CF.

U.S. Pat. No. 7,495,103 discloses modulators of ATP-binding cassette transporters such as ivacaftor and also discloses methods of treating CFTR transporter mediated diseases using such modulators.

U.S. Pat. No. 8,324,242 describes a method of treating or lessening the severity of cystic fibrosis in a patient, said method comprising the step of administering to said patient an effective amount of ivacaftor, wherein the patient possesses a cystic fibrosis transmembrane receptor with a G551D mutation.

U.S. Pat. No. 8,354,427 describes a method of treating or lessening the severity of cystic fibrosis in a patient, wherein said patient possess a cystic fibrosis transmembrane receptor (CFTR) with a R117H mutation, said method comprising the step of administering to said patient an effective amount of ivacaftor.

U.S. Pat. No. 8,629,162 describes a method of treating or lessening the severity of a moderate to mild clinical phenotype of cystic fibrosis in a patient, said method comprising the step of administering to said patient a pharmaceutical composition comprising ivacaftor.

U.S. Pat. No. 8,754,224 describes a solid dispersion comprising amorphous ivacaftor and a polymer, wherein the polymer is polyvinylpyrrolidone (PVP), polyvinyl alcohols (PVA), polymethacrylate, β-cyclodextrin, or vinylpyrrolidone/vinyl acetate copolymer (PVP/VA). It also describes crystal form A, crystal form B and amorphous form of ivacaftor.

U.S. Pat. No. 8,471,029 discloses crystalline form C of ivacaftor, pharmaceutical compositions thereof and methods therewith.

U.S. Pat. No. 8,674,108 discloses crystalline solvate forms of ivacaftor, which are designated as Form D, Form E, Form F, Form G, Form H, Form I, Form J, Form K, Form L, Form M, Form N, Form O, Form P, Form Q, Form R, Form S, Form T, Form W and hydrate B and methods for their preparation. It further discloses pharmaceutical compositions comprising the crystalline solvate forms of ivacaftor, as well as methods of treatment therewith.

U.S. Pat. No. 8,163,772 discloses solid forms of ivacaftor which are co-forms, for example, salts, solvates, co-crystals and hydrates of ivacaftor. It describes Ivacaftor co-forms with 2-methylbutyric acid, propylene glycol, PEG400.KOAc, lactic acid, isobutyric acid, propionic acid, ethanol, 2-propanol, water, besylate, hemibesylate, and besylate monohydrate.

U.S. Pat. No. 8,883,206 describes pharmaceutical compositions containing a solid dispersion of ivacaftor with HPMCAS and one or more of the excipients selected from one or more fillers, a sweetener, a disintegrant, a wetting agent, a glidant, and a lubricant. The said pharmaceutical composition of the solid dispersions formulated into powders, granules and mini-tablets. It also describes methods for manufacturing and processing the powders, granules and mini-tablets, and methods for treating cystic fibrosis employing the pharmaceutical composition.

U.S. Publication No. 2014/0221424 describes pharmaceutical composition of ivacaftor use in the treatment of cystic fibrosis, wherein said composition is in the form of tablets obtain by spray dried dispersion technique.

U.S. Pat. No. 7,553,855 discloses a pharmaceutical composition comprising ivacaftor, PEG 400, and PVP K30.

U.S. Publication No. 2015/0010628 discloses a pharmaceutical composition comprising a solid dispersion of amorphous or substantially amorphous ivacaftor, a filler, a sweetener, a disintegrant, a glidant and a lubricant, and optionally a wetting agent.

PCT Publication No. 2016/199085 discloses nanoparticulate compositions of ivacaftor or a pharmaceutically acceptable salt thereof, and methods of making and using such compositions. The said compositions comprise ivacaftor particles having an effective average particle size of less than about 2000 nm, at least one surface stabilizer and optionally one or more pharmaceutically acceptable excipients.

Currently, Ivacaftor is marketed as Tablets in strength of 75 mg and 150 mg and Oral granules in strength of 25 mg, 50 mg and 75 mg per packet under the trade name KALYDECO® which is a cystic fibrosis transmembrane conductance regulator (CFTR) potentiator indicated for the treatment of cystic fibrosis (CF) in patients age 12 months and older who have one mutation in the CFTR gene.

The solid dosage forms are difficult to swallow, especially for paediatric and geriatric patients. Further, the fear of swallowing or choking on such solid shaped forms is still a concern in certain populations. However, administration of oral granules may be associated with an issue of incomplete dosing. The patient compliance is often a problem with oral solid dosage forms, especially with young paediatrics and geriatrics patients.

Therefore, there is need in the art to develop stable oral liquid solution of ivacaftor for the treatment of cystic fibrosis (CF) in patients age 12 months and older who have one mutation in the CFTR gene. The oral liquid solution is beneficial for administration specifically in paediatrics, geriatrics along with institutionalized patients and patients with physical disabilities or incapacitated, nausea, vomiting and motion sickness complications.

The drug administered in oral liquid solution dosage form is immediately available for absorption from the gastrointestinal tract and can be absorbed faster than the same amount of drug administered in a tablet or capsule. Therefore, the inventors of present application developed a stable oral liquid solution of ivacaftor which can obviate the problems associated with prior art and increases patient compliance.

SUMMARY OF THE INVENTION

The object of the invention is to develop a stable oral liquid solution of ivacaftor for the treatment of cystic fibrosis, providing flexibility in dosage regimes for patients who need special doses of the drug, specifically in paediatrics, geriatrics along with institutionalized patients and patients with complications for swallowing.

A first aspect of the present invention is to provide a stable oral liquid solution comprising a therapeutically effective amount of ivacaftor, and a pharmaceutically acceptable combination of excipients in an amount sufficient for oral liquid solution dosage form.

Another aspect of the present invention is to provide a stable oral liquid solution of ivacaftor, wherein the composition comprises:
  a) a therapeutically effective amount of ivacaftor or a pharmaceutically acceptable salt or solvate thereof, and
  b) a solvent system selected from group consisting of Polyethylene Glycols 400 and or Hydrogenated Vegetable Oil used individually or in combination thereof.

Another aspect of the present invention is to provide a stable oral liquid solution of ivacaftor, wherein the composition comprises:
  a) a therapeutically effective amount of ivacaftor or a pharmaceutically acceptable salt or solvate thereof;
  b) a solvent system selected from group consisting of Polyethylene Glycols 400 and or Hydrogenated Vegetable Oil used individually or in combination thereof,
  c) a solvent or cosolvent system selected from group consisting of either Glycerol, polyols like sorbitol, maltitol, lactitol etc. or Polyoxylglycerides or Hydrogenated Vegetable Oil and or combination thereof,
  d) solubilizing agent; and
  e) other pharmaceutically acceptable excipients.

Another aspect of the present invention is to provide a stable oral liquid solution of ivacaftor, wherein the composition comprises:
  a) a therapeutically effective amount of ivacaftor or a pharmaceutically acceptable salt or solvate thereof;
  b) a solvent system selected from group consisting of Polyethylene Glycols 400 and or Hydrogenated Vegetable Oil used individually or in combination thereof,
  c) a solvent or cosolvent system selected from group consisting of either Glycerol, polyols like sorbitol, maltitol, lactitol etc. or Polyoxylglycerides or Hydrogenated Vegetable Oil and or combination thereof,
  d) solubilizing agent; and
  e) other pharmaceutically acceptable excipients selected from group consisting of antioxidants, antimicrobial preservatives, sweetening agents, flavoring agents, coloring agents, buffering agents and the like.

Another aspect of the present invention is to provide a process for the preparation of a stable oral liquid solution comprising of ivacaftor and pharmaceutically acceptable excipients.

Another aspect of the present invention is to provide a method for treating or lessening the severity of cystic fibrosis in a patient who has difficulty in swallowing, comprising administering a pharmaceutically effective dose of an oral liquid solution of Ivacaftor.

DETAIL DESCRIPTION OF THE INVENTION

In one embodiment the present invention provides a stable oral liquid solution comprising a therapeutically effective amount of ivacaftor, and a pharmaceutically acceptable combination of excipients in an amount sufficient for oral liquid solution dosage form.

In another embodiment the present invention provides a stable oral liquid solution of ivacaftor, wherein the composition comprises:
  a) a therapeutically effective amount of ivacaftor or a pharmaceutically acceptable salt or solvate thereof, and
  b) a solvent system selected from group consisting of Polyethylene Glycols 400 and or Hydrogenated Vegetable Oil used individually or in combination thereof.

In another embodiment the present invention provides a stable oral liquid solution of ivacaftor, wherein the composition comprises:
  a) a therapeutically effective amount of ivacaftor or a pharmaceutically acceptable salt or solvate thereof;
  b) a solvent system selected from group consisting of Polyethylene Glycols 400 and or Hydrogenated Vegetable Oil used individually or in combination thereof,
  c) a solvent or cosolvent system selected from group consisting of either Glycerol, polyols like sorbitol, maltitol, lactitol etc. or Polyoxylglycerides or Hydrogenated Vegetable Oil and or combination thereof,
  d) solubilizing agent; and
  e) other pharmaceutically acceptable excipients.

In another embodiment the present invention provides a stable oral liquid solution of ivacaftor, wherein the composition comprises:
  a) a therapeutically effective amount of ivacaftor or a pharmaceutically acceptable salt or solvate thereof;

b) a solvent system selected from group consisting of Polyethylene Glycols 400 and or Hydrogenated Vegetable Oil used individually or in combination thereof,
c) a solvent or cosolvent system selected from group consisting of either Glycerol, polyols like sorbitol, maltitol, lactitol etc. or Polyoxylglycerides or Hydrogenated Vegetable Oil and or combination thereof,
d) solubilizing agent; and
e) other pharmaceutically acceptable excipients selected from group consisting of antioxidants, antimicrobial preservatives, sweetening agents, flavoring agents, coloring agents, buffering agents and the like.

"Ivacaftor" as used herein refers to N-(2,4-di-tert-butyl-5-hydroxyphenyl)-1,4-dihydro-4-oxoquinoline-3-carboxamide, as well as a pharmaceutically acceptable salt or solvate thereof.

A "therapeutically effective amount" of Ivacaftor is an amount of Ivacaftor or its pharmaceutically acceptable salts or solvate thereof which eliminates, alleviates, or provides relief of the symptoms for which it is administered.

As used in this specification, the singular forms "a", "an", and "the" include plural references unless the context clearly dictates otherwise. Thus, for example, a reference to "a method" "a process" includes one or more methods or processes, and/or steps of the type described herein and/or which will become apparent to those persons skilled in the art upon reading this disclosure and so forth.

As used in this specification, the term "oral liquid solution", refers to a liquid preparation in which the therapeutic agent i.e. ivacaftor and or various excipients are dissolved in the chosen solvent system.

The example of Hydrogenated Vegetable Oil is selected from partially or fully hydrogenated oil such as Castor Oil, Peanut Oil, Corn Oil, Coconut Oil or Cottonseed Oil.

The examples of solubilizing agent may include but not limited to ammonium lauryl sulfate (ALS), sodium lauryl sulfate (SLS), sodium laureth sulfate, sodium myreth sulfate, quaternary ammonium salts: cetrimonium bromide (CTAB), cetylpyridiniumchloride (CPC), benzalkonium chloride (BAC), benzethonium chloride (BZT), phospholipids phosphatidylserine, phosphatidylethanolamine, phosphatidylcholine and sphingomyelins, Poloxamer, Tweens, Spans and the like with or without water.

The examples of antioxidants may include but not limited to Sodium sulphate, sodium metabisulphite, sodium formaldehyde, sulphoxylate, ascorbic acid, butylated hydroxytoluene (BHT), Butylated hydroxy anisole, propyl gallate, sodium citrate, citric acid, and the like.

The examples of antimicrobial preservatives may include but not limited to Sorbic acid and its salts, potassium sorbate, methyl parahydroxybenzoate (Methylparaben), propyl parahydroxybenzoate, sodium benzoate, propionic acid used individually or in combination thereof.

The examples of sweetening agents may include but not limited to Sucrose, acesulfame potassium, sucralose, sodium saccharin, aspartame, sorbitol, xylitol, Neotame, Ammoniated Glycyrrhizin, Monoammonium Glycyrrhizinate or a combination thereof.

The examples of flavoring agents may include but not limited to peppermint, grape, orange, lime oil, lemon, pineapple, berries, lavender, dill, spearmint, *eucalyptus*, ethyl vanillin, fruit Flavor, caramel Flavor or combination thereof.

The examples of coloring agents may include but not limited to Titanium dioxide, brilliant Blue, indigo tine, erythrosine, allura red, sunset yellow, tartrazine, aluminum blue lake or combination thereof.

The examples of buffering agents may include but not limited to citric acid, sodium citrate, trometamol and the like used individually or in combination thereof.

In another embodiment the present invention provides a process for the preparation of a stable oral liquid solution comprising of ivacaftor and pharmaceutically acceptable excipients.

In another embodiment the present invention provides a method for treating or lessening the severity of cystic fibrosis in a patient who has difficulty in swallowing, comprising administering a pharmaceutically effective dose of an oral liquid solution of Ivacaftor.

In another embodiment the present invention provides a stable oral liquid solution of ivacaftor having higher bio-availability under fasted and fed condition against existing marketed tablet formulation i.e. KALYDECO tablets.

It is contemplated that the pharmaceutical compositions described herein are stored in a glass bottle. In yet another embodiment, the enclosed, glass bottle has a volume of 150 ml or 300 ml.

The invention is further illustrated by the following examples which are provided merely to be exemplary of the invention and do not limit the scope of the present invention. Certain modifications and equivalents will be apparent to those skilled in the art and are intended to be included within the scope of the invention. However, these are not intended to limit the scope of the present invention in any way.

EXAMPLE 1

The following is an exemplary method of preparing oral liquid solution of Ivacaftor.

TABLE No. 1

General composition for oral liquid solution of Ivacaftor

| Sr. No. | Ingredients | % Concentration |
|---|---|---|
| 1. | Ivacaftor | 1-30% |
| 2. | Polyethylene Glycol | 10-99% |
| 3. | Sodium Lauryl Sulfate | 0.5-5% |
| 4. | Sucralose | 0.1-10% |
| 5. | Butylated Hydroxy anisole | 0.005-0.5% |
| 6. | Flavoring agent | 0.1-10% |
| 1. | Ivacaftor | 1-30% |
| 7. | Methylparaben | 0.015-0.2% |
| 8. | Glycerin | 1-50% |

Procedure: Polyethylene glycol is dispensed into a mixing tank, to it accurately weighed quantity of Ivacaftor API is added under continuous stirring. Weighed quantity of sodium lauryl sulfate is added and stirred to form a clear liquid. All other excipients are added in a sequential manner to this mixture and mixed until complete dissolution is achieved.

EXAMPLE 2

TABLE No. 2

General composition for oral liquid solution of Ivacaftor

| Sr. No. | Ingredients | % Concentration |
|---|---|---|
| 1. | Ivacaftor | 1-30% |
| 2. | Polyethylene Glycol | 10-99% |
| 3. | Sodium Lauryl Sulfate | 0.5-5% |
| 4. | Sucralose | 0.1-10% |

TABLE No. 2-continued

General composition for oral liquid solution of Ivacaftor

| Sr. No. | Ingredients | % Concentration |
|---|---|---|
| 5. | Butylated Hydroxy anisole | 0.005-0.5% |
| 6. | Flavoring agent | 0.1-10% |
| 7. | Methylparaben | 0.015-0.2% |
| 8. | Glycerin | 1-50% |
| 9. | Hydrogenated Vegetable Oil (Hydrogenated Castor Oil) | 10-99% |

Procedure: Polyethylene glycol is dispensed into a mixing tank, to it accurately weighed quantity of Ivacaftor API is added under continuous stirring. Weighed quantity of sodium lauryl sulfate is added and stirred to form clear mixture. All other excipients are added in a sequential manner to this mixture and mixed until complete dissolution is achieved.

EXAMPLE 3

The following is an exemplary method of preparing oral liquid solution of Ivacaftor.

TABLE No. 3

General composition for oral liquid solution of Ivacaftor

| Sr. No. | Ingredients | % Concentration |
|---|---|---|
| 1. | Ivacaftor | 1-30% |
| 2. | Hydrogenated Vegetable Oil (Hydrogenated Castor Oil) | 10-99% |
| 3. | Sodium Lauryl Sulfate | 0.5-5% |
| 4. | Sucralose | 0.1-10% |
| 5. | Butylated Hydroxy anisole | 0.005-0.5% |
| 6. | Flavoring agent | 0.1-10% |
| 7. | Methylparaben | 0.015-0.2% |
| 8. | Glycerin | 1-50% |

Procedure: Hydrogenated Vegetable Oil is dispensed into a mixing tank, to it accurately weighed quantity of Ivacaftor API is added under continuous stirring. Weighed quantity of sodium lauryl sulfate is added and stirred to form clear mixture. All other excipients are added in a sequential manner to this mixture and mixed until complete dissolution is achieved.

EXAMPLE 4

The following is an exemplary method of preparing oral liquid solution of Ivacaftor.

TABLE No. 4

General composition for oral liquid solution of Ivacaftor

| Sr. No. | Ingredients | % Concentration |
|---|---|---|
| 1. | Ivacaftor | 1-30% |
| 2. | Polyethylene Glycol | 40-99% |
| 3. | Sucralose | 0.1-10% |
| 4. | Butylated Hydroxy anisole | 0.005-0.5% |
| 5. | Methylparaben | 0.015-0.2% |
| 6. | Flavoring agent | 0.1-10% |
| 7. | Glycerin | 1-50% |
| 8. | Hydrogenated Vegetable Oil (Hydrogenated Castor Oil) | 10-99% |

Procedure: Polyethylene glycol is dispensed into a mixing tank, to it accurately weighed quantity of Ivacaftor API is added under continuous stirring. All other excipients are added in a sequential manner to this mixture and mixed until complete dissolution is achieved.

EXAMPLE 5

TABLE No. 5

General composition for oral liquid solution of Ivacaftor

| Sr. No. | Ingredients | % Concentration |
|---|---|---|
| 1. | Ivacaftor | 1-30% |
| 2. | Polyethylene Glycol | 10-99% |
| 3. | Sodium Lauryl Sulfate | 0.5-5% |
| 4. | Sucralose | 0.1-10% |
| 5. | Butylated Hydroxy anisole (BHA) | 0.005-0.5% |
| 6. | Methylparaben | 0.015-0.2% |
| 7. | Flavoring agent | 0.1-10% |
| 8. | Hydrogenated Vegetable Oil (Hydrogenated Castor Oil) | 10-99% |

Procedure: Polyethylene glycol is dispensed into a mixing tank, to it accurately weighed quantity of Ivacaftor API is added under continuous stirring. Weighed quantity of sodium lauryl sulfate is added and stirred to form clear mixture. All other excipients are added in a sequential manner to this mixture and mixed until complete dissolution is achieved.

EXAMPLE 6

TABLE No. 6

General composition for oral liquid solution of Ivacaftor

| Sr. No. | Ingredients | % Concentration |
|---|---|---|
| 1. | Ivacaftor | 1-30% |
| 2. | Polyethylene Glycol | 10-99% |
| 3. | Sodium Lauryl Sulfate | 0.5-5% |
| 4. | Sucralose | 0.1-10% |
| 5. | Butylated Hydroxy anisole (BHA) | 0.005-0.5% |
| 6. | Flavoring agent | 0.1-10% |
| 7. | Hydrogenated Vegetable Oil (Hydrogenated Castor Oil) | 10-99% |

Procedure: Polyethylene glycol is dispensed into a mixing tank, to it accurately weighed quantity of Ivacaftor API is added under continuous stirring. Weighed quantity of sodium lauryl sulfate is added and stirred to form clear mixture. All other excipients are added in a sequential manner to this mixture and mixed until complete dissolution is achieved.

EXAMPLE 7

TABLE No. 7

General composition for oral liquid solution of Ivacaftor

| Sr. No. | Ingredients | % Concentration |
|---|---|---|
| 1. | Ivacaftor | 1-30% |
| 2. | Polyethylene Glycol | 10-99% |
| 3. | Sodium Lauryl Sulfate | 0.5-5% |
| 4. | Sucralose | 0.1-10% |
| 5. | Methylparaben | 0.015-0.2% |

TABLE No. 7-continued

General composition for oral liquid solution of Ivacaftor

| Sr. No. | Ingredients | % Concentration |
|---|---|---|
| 6. | Flavoring agent | 0.1-10% |
| 7. | Hydrogenated Vegetable Oil (Hydrogenated Castor Oil) | 10-99% |

Procedure: Polyethylene glycol is dispensed into a mixing tank, to it accurately weighed quantity of Ivacaftor API is added under continuous stirring. Weighed quantity of sodium lauryl sulfate is added and stirred to form clear mixture. All other excipients are added in a sequential manner to this mixture and mixed until complete dissolution is achieved.

EXAMPLE 8

The following is an exemplary method of preparing oral liquid solution of Ivacaftor.

TABLE No. 8

Specific composition for oral liquid solution of Ivacaftor

| Sr. No. | Ingredients | Concentration/5 ml |
|---|---|---|
| 1. | Ivacaftor | 150 mg |
| 2. | Polyethylene Glycol | 2.5 ml |
| 3. | Hydrogenated Vegetable Oil (Hydrogenated Castor Oil) | q.s. |
| 4. | Sucralose | 200 mg |
| 5. | Sodium Lauryl Sulfate | 96 mg |
| 6. | Methyl Parahydroxybenzoate | 7.5 mg |
| 7. | Butylated Hydroxy anisole (BHA) | 0.05 mg |
| 8. | Flavoring agent | 100 mg |

Procedure: Polyethylene glycol is dispensed into a mixing tank, to it accurately weighed quantity of Ivacaftor API is added under continuous stirring. Weighed quantity of sodium lauryl sulfate is added and stirred to form clear mixture. All other excipients are added in a sequential manner to this mixture and mixed until complete dissolution is achieved.

EXAMPLE 9

The following is an exemplary method of preparing oral liquid solution of Ivacaftor.

TABLE No. 9

Specific composition for oral liquid solution of Ivacaftor

| Sr. No. | Ingredients | Concentration/5 ml |
|---|---|---|
| 1. | Ivacaftor | 150 mg |
| 2. | Polyethylene Glycol | 4273 mg |
| 3. | Glycerin | q.s. |
| 4. | Sucralose | 100 mg |
| 5. | Methyl Parahydroxybenzoate | 7.5 mg |
| 6. | Butylated Hydroxy anisole (BHA) | 0.05 mg |
| 7. | Flavoring agent | 100 mg |

Procedure: Polyethylene glycol is dispensed into a mixing tank, to it accurately weighed quantity of Ivacaftor API is added under continuous stirring. Weighed quantity of other ingredients were added and stirred to form clear mixture. All other excipients are added in a sequential manner to this mixture and mixed until complete dissolution is achieved.

Observed stability data for the Example 8 composition packed in glass bottle, under accelerated and long-term storage are reported in Tables 10.

| | | | Stability Tests | | | | | |
|---|---|---|---|---|---|---|---|---|
| Parameter | Specification | Initial | 40° C./ 75% RH 3M | 40° C./ 75% RH 6M | 25° C./ 60% RH 3M | 25° C./ 60% RH 6M | 30° C./ 65% RH 3M | 30° C./ 65% RH 6M |
| Description | Clear Liquid Solution | | | | Comply | | | |
| Assay (%) | 90.0%-110.0% | 100.1 | 101.1 | 98.8 | 102.2 | 98.9 | 99.6 | 99.4 |
| Specific Gravity | For Information Purpose only | 1.1047 | 1.1102 | 1.1086 | 1.1060 | 1.1055 | 1.1062 | 1.1059 |
| Related Substances (%) | Acid Impurity | NMT 0.20 % | ND | ND | ND | ND | ND | ND | ND |
| | Nitro phenol Impurity | NMT 0.20% | ND | ND | ND | ND | ND | ND | ND |
| | Ethyl ester impurity | NMT 0.20% | ND | ND | ND | ND | ND | ND | ND |
| | Amine impurity | NMT 0.20% | ND | ND | ND | ND | ND | ND | ND |
| | 3,5, Ivacaftor impurity | NMT 0.20% | ND | ND | ND | ND | ND | ND | ND |
| | Single Maximum Unknown impurity | NMT 0.20% | 0.01 | 0.05 | 0.05 | 0.05 | 0.06 | 0.03 | 0.04 |
| | Total Impurities | NMT 1.5% | 0.01 | 0.12 | 0.19 | 0.13 | 0.21 | 0.16 | 0.18 |

\* ND: Not detected
\*NMT: Not More Than

Bioavailability Study:

Bioavailability Study was performed for oral liquid solution of Ivacaftor and the observed pharmacokinetic parameters are summarized below:

1. Randomized, Open Label, Balanced, Single-Dose, Two-Treatment, Two-Period, Two-Sequence, Two-Way Crossover bioavailability study under fed condition:

| Parameters | Least Squares Geometric Means for R Kalydeco ® tablet 150 mg | Least Squares Geometric Means for T1 (Ivacaftor Oral Solution 150 mg/5 ml) | Least Squares Geometric Means Ratio (T1/R) |
|---|---|---|---|
| Ivacaftor Oral Solution 150 mg/5 ml (T1) vs Kalydeco ® tablet 150 mg Fed Condition | | | |
| $AUC_{0-t}$ (hr * ng/ml) | 11742.720 | 15271.194 | 130.05 |
| $AUC_{0-\infty}$ (hr * ng/ml) | 12504.667 | 16098.450 | 128.74 |

2. Randomized, Open Label, Balanced, Single-Dose, Two-Treatment, Two-Period, Two-Sequence, Two-Way Crossover bioavailability study under fasted condition:

| Parameters | Least Squares Geometric Means for R Kalydeco ® tablet 150 mg | Least Squares Geometric Means for T1 (Ivacaftor Oral Solution 150 mg/5 ml) | Least Squares Geometric Means Ratio (T1/R) |
|---|---|---|---|
| Ivacaftor Oral Solution 150 mg/5 ml (T1) vs Kalydeco ® tablet 150 mg Fasted Condition | | | |
| $AUC_{0-t}$ (hr * ng/ml) | 5925.859 | 18060.463 | 304.77 |
| $AUC_{0-\infty}$ (hr * ng/ml) | 6379.788 | 18987.054 | 297.61 |

From above bioavailability study, it is observed that oral liquid solution of Ivacaftor has significantly higher bioavailability under fasted and fed condition.

We claim:

1. A liquid composition comprising:
    (a) a solvent system comprising a polyethylene glycol and a hydrogenated vegetable oil; and
    (b) a therapeutically effective amount of ivacaftor of Formula I:

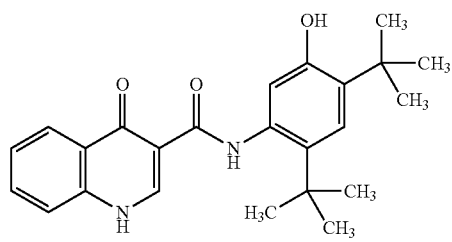

Formula I or a pharmaceutically acceptable salt thereof;
    wherein the liquid composition is formulated for oral administration.

2. The liquid composition of claim 1, wherein the polyethylene glycol is polyethylene glycol 400.

3. The liquid composition of claim 1, wherein the hydrogenated vegetable oil is a partially hydrogenated vegetable oil or a fully hydrogenated vegetable oil.

4. The liquid composition of claim 1, wherein the hydrogenated vegetable oil is selected from the group consisting of hydrogenated castor oil, hydrogenated coconut oil, hydrogenated corn oil, hydrogenated cottonseed oil, and hydrogenated peanut oil, or any combination thereof.

5. The liquid composition of claim 1, wherein the hydrogenated vegetable oil is hydrogenated castor oil.

6. The liquid composition of claim 1, wherein the liquid composition further comprises:
    (c) a cosolvent system or an additional solvent system selected from the group consisting of a polyol and a polyoxylglyceride, or any combination thereof;
    (d) a solubilizing agent; and
    (e) one or more pharmaceutically acceptable excipients independently selected from the group consisting of an antimicrobial preservative, an antioxidant, a buffering agent, a coloring agent, a flavoring agent, and a sweetening agent, or any combination thereof.

7. The liquid composition of claim 6, wherein the polyol is glycerol.

8. The liquid composition of claim 6, wherein the solubilizing agent is selected from the group consisting of ammonium lauryl sulfate (ALS), cetylpyridinium chloride (CPC), a quaternary ammonium salt, phosphatidylcholine (PC), phosphatidylethanolamine (PE), phosphatidylserine (PS), a phospholipid, a poloxamer, sodium laureth sulfate, sodium lauryl sulfate (SLS), sodium myreth sulfate, a Span, a sphingomyelin, and a Tween, or any combination thereof.

9. The liquid composition of claim 8, wherein the quaternary ammonium salt is selected from the group consisting of benzalkonium chloride (BAC), benzethonium chloride (BZT), and cetyltrimethylammonium bromide (CTAB).

10. The liquid composition of claim 6, wherein the solubilizing agent is sodium lauryl sulfate (SLS).

11. The liquid composition of claim 6, wherein the antimicrobial preservative is selected from the group consisting of methyl parahydroxybenzoate (methylparaben), propyl parahydroxybenzoate (propyl paraben), propionic acid, sodium benzoate, sorbic acid, and a salt of sorbic acid, or any combination thereof.

12. The liquid composition of claim 11, wherein the salt of sorbic acid is potassium sorbate.

13. The liquid composition of claim 6, wherein the antimicrobial preservative is selected from the group consisting of methyl parahydroxybenzoate (methylparaben), propyl parahydroxybenzoate (propyl paraben), and sodium benzoate, or any combination thereof.

14. The liquid composition of claim 6, wherein the antioxidant is selected from the group consisting of ascorbic acid, butylated hydroxyanisole (BHA), butylated hydroxytoluene (BHT), citric acid, propyl gallate, sodium citrate, sodium formaldehyde sulfoxylate (SFS), sodium metabisulphite, and sodium sulphate, or any combination thereof.

15. The liquid composition of claim 6, wherein the antioxidant is selected from the group consisting of butylated hydroxyanisole (BHA) and butylated hydroxytoluene (BHT), or a combination thereof.

16. The liquid composition of claim 6, wherein the buffering agent is selected from the group consisting of citric acid, sodium citrate, and trometamol, or any combination thereof.

17. The liquid composition of claim 6, wherein the coloring agent is selected from the group consisting of allura red, aluminum blue lake, brilliant blue, erythrosine, indigo tine, sunset yellow, tartrazine, and titanium dioxide, or any combination thereof.

18. The liquid composition of claim 6, wherein the flavoring agent is selected from the group consisting of caramel flavor, dill oil, ethyl vanillin, a fruit flavor, *eucalyptus* oil, lavender, peppermint oil, and spearmint oil, or any combination thereof.

19. The liquid composition of claim 18, wherein the fruit flavor is selected from the group consisting of a berry, grape oil, lemon oil, lime oil, orange oil, and pineapple oil.

20. The liquid composition of claim 6, wherein the sweetening agent is selected from the group consisting of acesulfame potassium, ammoniated glycyrrhizin, aspartame, monoammonium glycyrrhizinate (MAG), Neotame, sodium saccharin, sorbitol, sucralose, sucrose, and xylitol, or any combination thereof.

21. The liquid composition of claim 6, wherein the liquid composition further comprises:
(a) a solvent system comprising polyethylene glycol 400 and hydrogenated vegetable oil;
(b) a therapeutically effective amount of ivacaftor of Formula I:

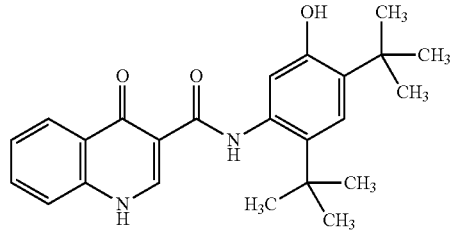

Formula I or a pharmaceutically acceptable salt thereof;
(c) a cosolvent system or an additional solvent system selected from the group consisting of a polyol and a polyoxylglyceride, or any combination thereof;
(d) a solubilizing agent which is sodium lauryl sulfate;
(e1) an antimicrobial preservative selected from the group consisting of methyl parahydroxybenzoate (methylparaben), propyl parahydroxybenzoate (propyl paraben), and sodium benzoate, or any combination thereof; and
(e2) an antioxidant selected from the group consisting of butylated hydroxyanisole (BHA) and butylated hydroxytoluene (BHT), or a combination thereof.

22. The liquid composition of claim 6, wherein the liquid composition is packed in a glass bottle.

23. A method for lessening the severity of cystic fibrosis in a patient who has difficulty in swallowing, wherein the method comprises administering to the patient in need thereof a therapeutically effective amount of the liquid composition of claim 1.

24. A method for treating cystic fibrosis in a patient who has difficulty in swallowing, wherein the method comprises administering to the patient in need thereof a therapeutically effective amount of the liquid composition of claim 1.

25. A liquid composition comprising:
(a) a solvent system comprising polyethylene glycol 400 and hydrogenated castor oil;
(b) a therapeutically effective amount of ivacaftor of Formula I:

Formula I or a pharmaceutically acceptable salt thereof;
(c) a solubilizing agent which is sodium lauryl sulfate;
(d) an antimicrobial preservative which is methyl parahydroxybenzoate (methylparaben); and
(e) an antioxidant which is butylated hydroxyanisole (BHA);
wherein the liquid composition is formulated for oral administration.

* * * * *